United States Patent [19]

McClure

[11] Patent Number: 4,552,779

[45] Date of Patent: Nov. 12, 1985

[54] PROCESS FOR PREPARING A CAST METAL SURFACE STRUCTURE FOR BONDING TO A TOOTH STRUCTURE AND MATERIAL USED THEREWITH

[75] Inventor: Scott G. McClure, Fallbrook, Calif.

[73] Assignee: Douglass B. Roberts, Loma Linda, Calif. ; a part interest

[21] Appl. No.: 555,644

[22] Filed: Nov. 28, 1983

[51] Int. Cl.[4] .......................... A01N 1/02; C09K 3/00; A61C 13/22

[52] U.S. Cl. .......................................... 427/2; 106/35; 264/17; 433/191; 433/200.1; 433/206; 433/208

[58] Field of Search .................................... 264/17–19; 433/191, 200, 206, 207, 208; 427/2; 106/35

[56] References Cited

U.S. PATENT DOCUMENTS

| | | | |
|---|---|---|---|
| 3,578,493 | 5/1971 | Smith | 427/391 X |
| 4,172,323 | 10/1979 | Orlowski | 433/191 |
| 4,269,595 | 5/1981 | Nemethy | 264/17 X |
| 4,369,033 | 1/1983 | Webb et al. | 433/9 |

Primary Examiner—Michael R. Lusignan
Attorney, Agent, or Firm—Harvey S. Hertz

[57] ABSTRACT

A process for preparing a cast metal surface such that it is usable for bonding to a tooth structure. A water soluble adhesive medium is placed on a stone cast of a tooth or teeth. A mixture of soluble and non-soluble particles are then placed onto the adhesive. The soluble particles partially dissolve into the adhesive medium while the non-soluble particles adhere to the adhesive. Wax or resin is flowed over the resultant surface to imbed the particles therein. The desired tooth form is then completed after which the adhesive is dissolved away to release the pattern from the cast. The remaining soluble particles are then washed away leaving voids in the surface of the pattern. These voids are then duplicated using standard lost wax casting procedures to reproduce the surface in metal. The surface, which has a multiplicity of voids, roughnesses, and undercuts, is then filled with a bonding medium to attach the rigid cast metal appliance to a tooth surface.

7 Claims, 5 Drawing Figures

PROCESS FOR PREPARING A CAST METAL SURFACE STRUCTURE FOR BONDING TO A TOOTH STRUCTURE AND MATERIAL USED THEREWITH

BACKGROUND OF THE INVENTION (1) Field of the Invention

The invention relates generally to the bonding of a dental bridge or appliance to a tooth and more particularly, to a process for preparing a metal surface for bonding to tooth structure as well as an adhesive used in conjunction with soluable and nonsoluable particles to form voids in a pattern for a metal retaining structure.

(2) Description of the Prior Art

When preparing a dental bridge that will replace a missing tooth between two adjacent teeth, the normal procedure is to drill the two adjacent teeth to a post-like shape and then cement the fabricated three-tooth bridge onto the two posts or abutment teeth.

One prior art technique for eliminating the cutting down of the adjacent teeth, is the Maryland-Type bridge. In this technique, etched metal (non-precious) pads secure the bridge to the teeth adjacent to the replacement tooth. Etching of the metal retainers is performed in an electrolytic bath. Etching creates a roughened surface (of microscopic proportions) enabling the pads to be secured (by resins) to the abutment teeth. The process increases the surface roughness needed to enable the bonding resin to be secured to the metal. The metal normally must be non-precious and the surface cannot be touched as it is very sensitive.

Another prior art technique utilizes the Unitek-Duralingual mesh. This technique has been found to be hard to use as it can only be used on convex, flat or slightly concave surfaces (two-dimensional).

One other prior art includes U.S. Pat. Nos. 4,269,595; 4,172,323; 2,936,490; 2,152,069; 2,672,686; 3,369,297; and 726,381.

SUMMARY OF THE INVENTION

A process for preparing a metal retaining surface structure such that it is usable for bonding to tooth structure. The process includes the steps of using a wax or resin pattern having a surface roughness which, after being cast in metal, allows the bonding medium to be flowed or pressed into spaces in the metal surface enabling the metal surface to be attached to the tooth surface.

A soluble adhesive medium is placed on a stone cast of a tooth or teeth. Particles are then partially dissolved into the adhesive medium. Wax or resin is flowed over the resultant surface to imbed the particles therein. The shape of the desired tooth form is then completed with wax or resin after which the adhesive and the remaining soluble particles are dissolved out of the wax or resin pattern leaving voids in the pattern. These void are then duplicated with casting investment material which is flowed or poured around the wax or resin pattern. After the investment material has hardened, the pattern is burned or melted out of the casting investment and molten metal poured into the investment. When the metal solidifies, the casting investment material is removed from the surface of the metal, leaving a metal surface that has a multiplicity of voids, roughness, and undercuts which will be filled with a bonding medium for attaching the cast metal appliance to a tooth surface. The soluble adhesive medium is typically a water-soluble (waterbase) adhesive. The water soluble medium enables soluble crystals to partially dissolve into the adhesive in order to create the interface for the investment to enter into and hold the nonsoluble particles (beads) in position.

DESCRIPTION OF THE PREFERRED EMBODIMENTS

Figure 1:
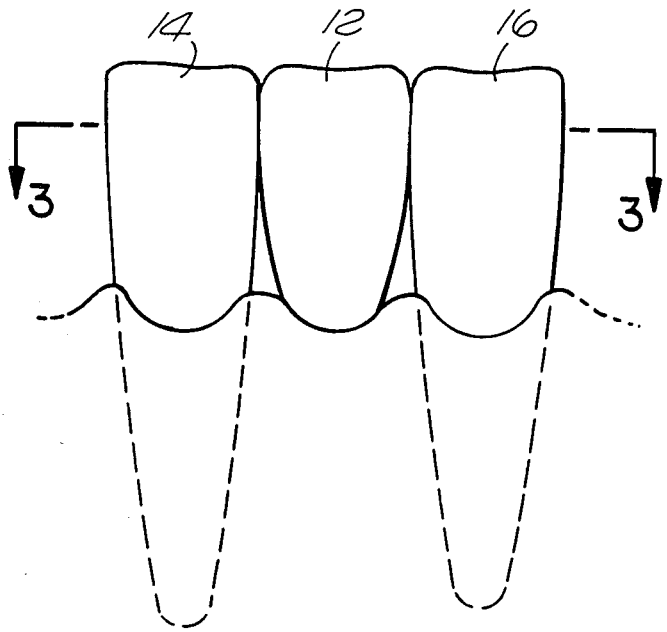
FIG. 1 is a fragmentary elevational view of the human lower jaw shown from the facial side with a pontic secured in place in accordance with the invention.
Figure 2:
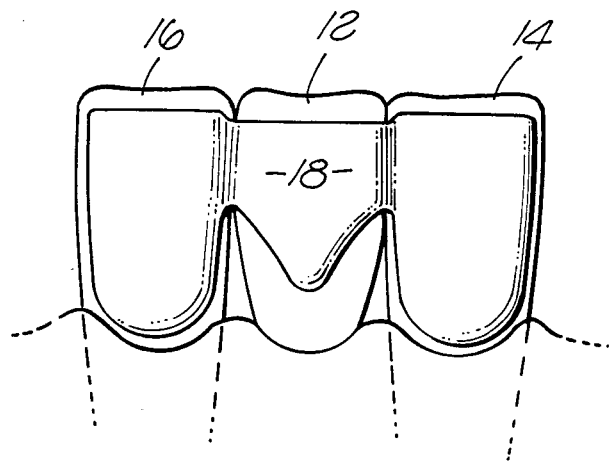
FIG. 2 is a fragmentary elevational view of the jaw of FIG. 1 shown from the lingual side.
Figure 3:
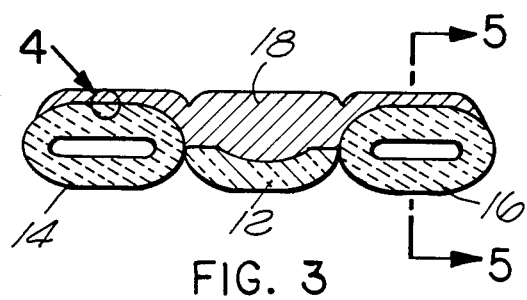
FIG. 3 is a cross-sectional view taken along the line 3—3 of FIG. 1.
Figure 5:
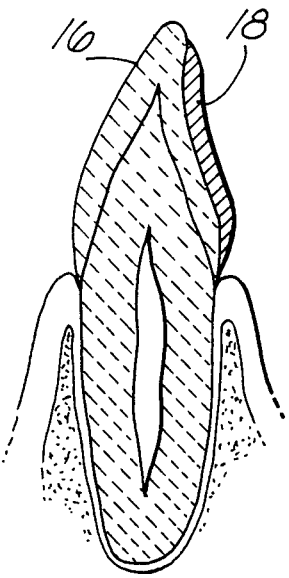
FIG. 5 is a cross-sectional view taken along the line 5—5 of FIG. 3.

Referring now to the drawings, there is shown in FIG. 1 a pontic 12 secured or attached between a pair of natural or abutment teeth 14 and 16. FIG. 1 illustrates the facial view of the pontic 12 and abutment teeth 14 and 16. The lingual view of these teeth are shown in FIG. 2, with a metal retainer 18 illustrated to secure the pontic 12 to the pair of abutment teeth 14 and 16.

The present invention relates to the method and material used to create the bonding surface of the metal retainer 18 to the abutment teeth 14 and 16.

As in the normal preparation of a dental bridge utilizing the lost wax casting technique, an impression is made in a tray of the patient's mouth, including the teeth or tooth to be restored. Then a cast (occasionally referre to as a stone cast), is made from the impression in the tray. This cast is a duplicate of the portion of the mouth into which the prosthesis is to be fitted. The cast is allowed to dry thoroughly before the process of making the pattern is begun.

The pattern is an exact duplicate of the metal portion of the prosthesis which will eventually be placed in the mouth and secured to the patient's natural teeth.

After the cast has been allowed to dry thoroughly, typically for 24 hours, a soluble adhesive (to be described in greater detail herein after) is painted on the cast in areas selected for retention on the abutment teeth 14 and 16. A small brush is normally used so that a very thin layer of the adhesive can be applied on the cast.

Then a mixture of soluble and nonsoluble particles (which will be described in greater detail herein after) is pressed into the soluble adhesive such as by lightly packing with the finger. The particles form a thin layer no thicker than the diameter of the nonsoluble particles as the soluble particles partially dissolve. After the adhesive is allowed to dry for a few minutes, a wax with a relatively low fusing temperature or a resin is flowed into the surface of the mixture of soluble and nonsoluble particles. The wax or resin should not extend beyond the area covered by the soluble adhesive.

After the soluble and nonsoluble particles have been covered with the thin layer of wax or resin, the remainder of the tooth cast is covered with a lubricating medium which allows subsequent applications of wax or resin to be placed on the tooth cast, while simultaneously preventing the wax or resin from adhering to the tooth cast. The shape of the desired tooth form is then completed by added and carving the wax to the desired shape. After the desired tooth form has been achieved, casting sprues are attached to the pattern and the cast is soaked in room temperature water for approximately 30–45 minutes so that it absorbs water and subsequently dissolves the adhesive which is painted on the surface of the tooth cast. Then the wax or resin can be removed from the tooth cast by gently pulling the pattern away from the cast.

The retentive areas of the pads which have been formed adjacent the abutment teeth 14 and 16 are washed directly with a gentle stream of room-temperature water to wash off the remaining adhesive and soluble particles, exposing non-soluble beads and voids. The pattern is then cleaned and dried thoroughly.

Then the wax pattern is attached to a crucible former and hard investment such as phosphate bound investment material is poured around the wax pattern. It is important that the investing material be forced into the voids and irregularities in the wax pattern on the tooth side of the pattern.

The investment is placed in a furnace at a temperature sufficiently high (typically, 1000° F. to 1700° F.) to burn the insoluble particles and melt or burn away the wax or resin leaving the investment mold into which molten metal is poured in order to create an exact duplicate of the wax or resin pattern which is made on the tooth cast. After the metal casting is removed from the investment material, it is cleaned and the portion of the casting which is exposed in the mouth is polished. At this time any materials used to enhance or develop the esthetic requirements (such as porcelain or plastic) are added to the metal casting.

Figure 4:
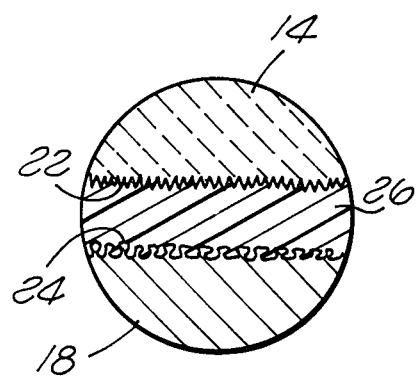
FIG. 4 is an enlarged fragmentary view of that area encompassed by the circle 4 of FIG. 3.

The casting is then placed in the patient's mouth to check for proper fit. When proper fit has been obtained, the tooth is isolated from any fluids in the oral cavity and treated with an acid solution which de-mineralizes the surface 22 of the teeth 14 and 16, as can be seen in FIG. 4, creating microscopic roughness on the tooth 16 surface 22 adjacent to the metal retainer voids 24. After the acid is washed from the tooth and the tooth is throughly dried, the prosthesis is then attached to the tooth with a bonding resin 26 which flows into the microscopic roughness on the tooth and into the voids and undercuts on the tooth side of the metal casting. As the resin hardens, it bonds the prosthesis to the tooth.

The soluble adhesive, which is painted on the cast in the area selected for retention, typically can be formed in one preferred embodiment of approximately three parts conventional white glue such as Elmers Glue manufactured by Borden, Inc., one part saturated solution of crystals, one part water, and coloring agent.

The mixture of soluble and insoluble particles which is pressed into the soluble adhesive typically is formed of the following:
1. Hexamethylenetetramine Crystals (soluble particles).
2. Small nylon or resin beads approximately 0.4 mm in diameter (nonsoluble particles).

The crystal bend mixture has been found to be preferable to be 50% of each by volume. The granular size is determined by the bead size. All crystals are ground to bead size or smaller. The crystals sublimate below casting temperature. Therefore, there is no porosity in the casting if a soluble crystal is retained in the wax after investing. It has been found that the adhesive and the crystals coalesce to create a space for the investment to enter after the adhesive and crystals have been dissolved. This process of coalescence is achieved by using a water-soluble (water-based) adhesive and a crystal that is water-soluble. The crystal actually partially dissolves in the adhesive. Without colescence, the wax will diffuse around the particle leaving a very small space for the investment to enter. Nylon or resin beads are pressed and fused into the adhesive and touch the surface of the stone cast so that when the crystals are washed out it will leave undercuts formed by the exposed beads and washed-out crystals. But the subsequent resulting cast metal surface will have points of contact on the stone and finally the abutment tooth.

The preferred embodiment or soluble and nonsoluble particle mix is approximately 50% of each by volume. However, it should be understood that various other combinations could be utilized.

The soluble component in the "crystal/bead mix" could be particles, crystals or any form that is soluble in the solvent used (i.e., $H_2O$, alcohol or any solvent that does not dissolve the pattern (nonsoluble component). The solvent used that dissolves the soluble component of the "crystal/bead mix" preferably should also be able to dissolve the adhesive binder used to place the mix on the cast. However, the solvent that dissolves the soluble particles and the solvent that dissolves the adhesive could be different depending on what the individual components of each are made of. $H_2O$ is normally the solvent of choice since it is common, inexpensive and has no side effect on the final pattern (except possibly for dimensional changes due to the temperature of the solvent). Therefore, it is recommended that room temperature solvent be used.

The soluble compound in the bead/crystal mix should be quite soluble. If there was a soluble component trapped in the pattern, the trapped soluble component should leave no residues if heated to casting temperatures (i.e., it should sublime, vaporize, burn, eliminate itself) so there would not be contamination in the final investment pattern after pattern is "burned out".

The soluble component of the bead/crystal mix can dissolve into the adhesive/binder slightly or the consistency of the adhesive can be such that it has maximum contact to the particles due to surface tension properties of the adhesive.

Alternate examples of possible soluble components of "bead/crystal mix" would be:
  granular sucrose ($H_2O$ soluble)
  d-Citramalic acid (dl) ($H_2O$ soluble)
  Pyrotartaric acid ($H_2O$ soluble)
  Tetramethyl succinic acid (alcohol soluble)

The nonsoluble particles in the "bead/crystal mix" should not be soluble in adhesive or solvent of soluble component of bead/crystal mix. (However, preferably solvent of soluble components and adhesive should be the same). They should burn out or be eliminated in heating with the rest of the pattern in the investment leaving no residues or contaminants in the investment.

Alternate examples of nonsoluble components would be:
1. Vinyl beads—particles
2. Resin beads—particles (Methyl Methacrylate)
3. Nylon beads—particles
4. Crystals (not soluble in solvent used)
5. Particles (not soluble in solvents used)
6. Walnut shells The preferred ratio of crystal to beads is 1.1 (50% to 50%). However satisfactory results have been achieved with crystal/beads ratios of from 30% crystal and 70% beads to 70% crystal and 30% beads.

I claim:

1. The method of preparing a metal surface of a cast metal appliance having a multiplicity of voids which can be filled with a bonding medium for attachment of said metal surface to a tooth surface comprising:
   making an impression of a patient's mouth;
   making a cast from said impression;
   placing an adhesive which is soluble in a predetermined fluid on the cast of a tooth;
   placing particles, a portion of which are soluble in said fluid, into the adhesive medium and imbedding the particles therein;
   flowing a wax or resin over the resultant surface to imbed said particles therein;
   dissolving out the adhesive and any soluble particles leaving voids in the pattern utilizing said fluid;
   duplicating the voids with casting investment material which is flowed or poured around the wax or resin pattern;
   burning or melting the pattern out of the casting investment;
   pouring molten metal into the investment; and
   removing the casting investment material from the said metal surface.

2. A method in accordance with claim 1 wherein both soluble and nonsoluble particles are placed into the adhesive medium.

3. A method in accordance with claim 2 wherein the layer of particles does not exceed the diameter of the nonsoluble particles.

4. A process for preparing a metal retaining surface structure such that it is usable for bonding to a tooth structure, the process wherein:
   an impression is made of a patient's mouth;
   a stone cast is made from said impression;
   an adhesive medium which is soluble in a predetermined fluid is placed on a stone cast;
   particles are placed into the adhesive, a portion of said particles being soluble in said fluid;
   a wax or resin is flowed over the resultant surface to imbed the particles therein; and
   the adhesive and remaining soluble particles being dissolved leaving voids which can be duplicated.

5. The process in accordance with claim 4 wherein the ratio of soluble to nonsoluble particles varies from a combination of 30% soluble particles and 70% nonsoluble particles to a combination of 70% soluble particles to 30% nonsoluble particles.

6. A mixture of particles, a portion of which is soluble in a predetermined fluid, for forming voids in a pattern which can be duplicated and filled with a bonding medium for attaching a resulting cast metal appliance having said voids to a tooth surface comprising:
   soluble particles varying from a minimum of 30% of said mixture to 70% of said mixture comprising a member of the group consisting of sucrose, malic acid, tartaric acid and succinic acid; and
   nonsoluble resin particles varying from 70% of said mixture to 30% of said mixture.

7. A mixture in accordance with claim 6 and further comprising an adhesive soluble in said predetermined fluid for adhering said mixture to a stone cast of a tooth.

* * * * *